United States Patent [19]
Orikasa

[11] Patent Number: 5,259,760
[45] Date of Patent: Nov. 9, 1993

[54] ORTHODONTIC ARCH WIRE

[75] Inventor: Masaaki Orikasa, Fukushima, Japan

[73] Assignee: Tomy K.K., Tokyo, Japan

[21] Appl. No.: 863,448

[22] Filed: Apr. 3, 1992

[30] Foreign Application Priority Data

Dec. 7, 1991 [JP] Japan ................................. 031207

[51] Int. Cl.⁵ .............................................. A61C 3/00
[52] U.S. Cl. ...................................................... 433/20
[58] Field of Search ............................... 433/20, 24

[56] References Cited

U.S. PATENT DOCUMENTS

| | | | |
|---|---|---|---|
| 4,412,819 | 11/1983 | Cannon | 433/20 |
| 4,424,033 | 1/1984 | Wool | 433/20 |
| 4,479,779 | 10/1984 | Wool | 433/20 |
| 4,818,226 | 4/1989 | Berendt et al. | 433/20 |
| 4,892,479 | 1/1990 | McKenna | 433/20 |
| 4,900,251 | 2/1990 | Andreasen | 433/20 |
| 5,017,133 | 5/1991 | Miura | 433/20 |
| 5,018,969 | 5/1991 | Andreiko et al. | 433/20 |
| 5,102,333 | 4/1992 | Suzuki et al. | 433/20 X |
| 5,137,446 | 8/1992 | Yoarauchi et al. | 433/20 |

*Primary Examiner*—Gene Mancene
*Assistant Examiner*—Nicholas D. Lucchesi
*Attorney, Agent, or Firm*—Kenyon & Kenyon

[57] ABSTRACT

An orthodontic arch wire is provided for applying corrective forces to a patient's dental arch. The orthodontic arch wire is an arch shaped wire capable of exerting forces on the dental arch that gradually vary in magnitude along the wire.

28 Claims, 6 Drawing Sheets

FORCE

FORCE

ORTHODONTIC ARCH WIRE

FIELD OF THE INVENTION

This invention relates generally to orthodontic devices and, more particularly, to orthodontic arch wires.

BACKGROUND INFORMATION

Orthodontic arch wires are commonly used in the field of orthodontics to apply corrective forces to misaligned teeth. The arch wires generally comprise a single wire formed into an arch shape corresponding to a patient's dental arch. When in use, the wire may be secured to the patient's teeth using a variety of devices, including brackets bonded to the teeth.

It is known that different teeth in the dental arch require application of different orthodontic forces for optimal root movement. For example, anterior teeth, canine to canine, require lighter forces than bicuspids and molars. Accordingly, arch wires have been segmented into separate sections corresponding to different teeth in the dental arch with each section of the arch wire capable of exerting distinctly different forces. For example, one section of the wire may correspond to the front or anterior teeth of a patient, a second section may correspond to the patient's bicuspids and a third section may correspond to the patient's molars. Each section is then provided with a distinctly different modulus of elasticity, which enables the wire to exert different forces on the different teeth in the dental arch.

However, because of age variations and other differences, dental arches and teeth size differ from patient to patient. General use of standard arch wires having a uniform segmentation of forces may be undesirable as it may result in orthodontic forces intended for shifting one set of teeth being unintentionally applied to another. For example, orthodontic forces intended for shifting bicuspids may be applied to the patient's molars. In addition, application of incorrect or unintended forces may result from slippage or movement of the arch wire after it has been placed in the patient's mouth.

Consequently, with prior art arch wires having a segmentation of forces, it may be necessary to have many different orthodontic arch wires to conform to the particular dental arches of individual patients.

An object of this invention is to provide generally standard orthodontic arch wires capable of exerting varying forces on teeth for obtaining proper root movement.

SUMMARY OF THE INVENTION

The present invention is directed to an orthodontic arch wire for applying corrective forces on a patient's dental arch. The arch wire comprises an arch shaped wire capable of exerting orthodontic forces on the dental arch that gradually and substantially continuously vary in magnitude along the wire.

One advantage of an arch wire having gradually and substantially continuously varying forces along the arch wire is that even with variations in a patient's dental arch and teeth size, the arch wire will provide generally suitable forces for proper root movement.

According to one embodiment of the invention, the arch wire has a gradually varying modulus of elasticity along the wire for enabling exertion of the gradually varying forces on the dental arch.

According to another embodiment of the invention, the orthodontic arch wire has a gradually varying cross sectional area along the wire for enabling exertion of gradually varying forces on the dental arch.

According to another embodiment of the invention, the arch wire has a rectangular cross section at the front of the arch wire and a circular cross section at the rear ends for providing reliable directional correction of front teeth and allowing smooth shifting of the arch wire during treatment.

According to another embodiment of the invention, the arch wire includes a stop member positioned on the front of the wire for enabling proper centering of the arch wire on the patient's dental arch and for deterring slippage.

A method is also provided for forming an arch wire capable of exerting gradually varying forces. The method includes the steps of subjecting an arch shaped wire to a heated medium and gradually removing the wire from the heated medium, thereby causing a gradual variation of the wire's modulus of elasticity.

BRIEF DESCRIPTION OF THE DRAWINGS

The foregoing and additional objects and advantages of the present invention will become more apparent in view of the following detailed description and drawings, in which like reference characters denote like parts.

DETAILED DESCRIPTION

Figure 1:
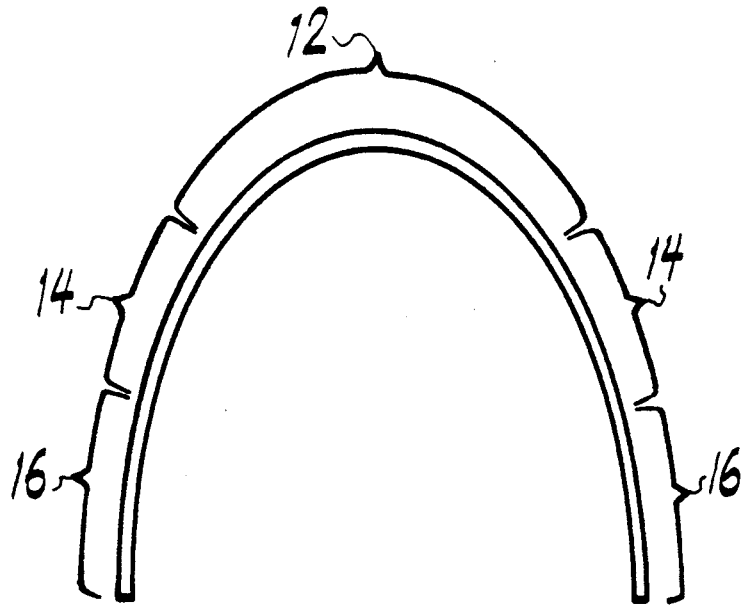
FIG. 1 is a top view of an orthodontic arch wire constructed in accordance with the prior art.

FIG. 1 is a top view of an arch wire 10 constructed in accordance with the prior art. The arch wire 10 is formed from a single wire into an arch shape corresponding to a dental arch. The arch wire 10 may comprise a nickel-titanium alloy wire having superelasticity. In use, the arch wire 10 may be secured to the patient's teeth with the use of brackets bonded to the teeth (not shown).

It is known that different teeth in the dental arch require different orthodontic forces for optimal root movement. For example, front or anterior teeth require smaller orthodontic forces than bicuspids or molars. Accordingly, the arch wire 10 is partitioned or segmented into a front section 12, two middle sections 14 and two rear end sections 16, which correspond to a patient's front teeth, bicuspids, and molars, respectively.

By selectively heat treating the arch wire 10, sections 12, 14 and 16 can each be provided with a distinctly different intrinsic modulus of elasticity, which enables the sections 12, 14 and 16 to exert distinctly different orthodontic forces when mounted on a dental arch.

Figure 2:
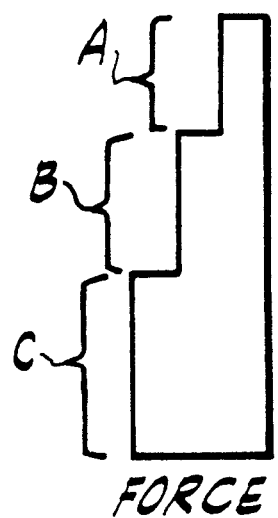
FIG. 2 illustrates the orthodontic force distribution of the arch wire shown in FIG. 1.

FIG. 2 illustrates the distribution of orthodontic forces along the arch wire 10. Reference characters A, B and C correspond to the forces exerted by sections 12, 14 and 16, respectively. As the figure shows, the orthodontic forces are stepped or vary distinctly from one section to the next. As an example of force magnitudes, reference characters A, B and C could refer to 100, 200 and 300 gram force levels, respectively.

Figure 3:
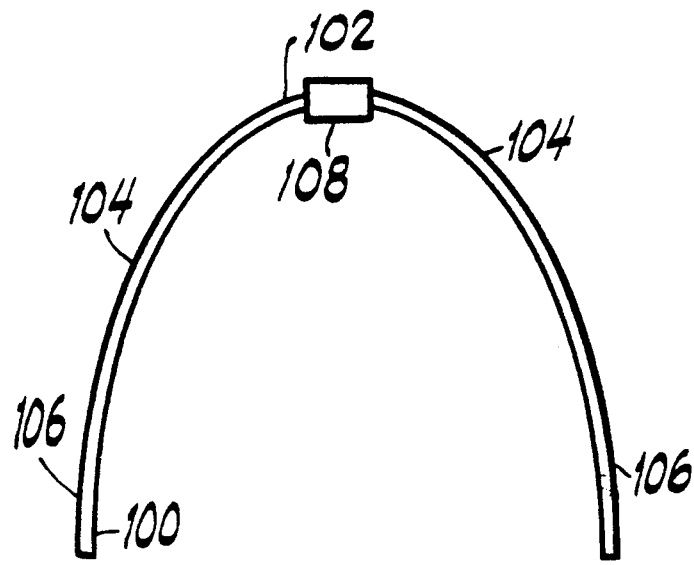
FIG. 3 is a top view of an orthodontic arch wire constructed in accordance with one embodiment of the invention.

FIG. 3 illustrates an arch wire 100 constructed in accordance with one embodiment of the present invention. The arch wire 100 includes a front section 102, two middle sections 104 and two rear end sections 106. When the arch wire 100 is mounted on a dental arch, the sections 102, 104 and 106 are generally positioned adjacent the patient's front teeth, bicuspids and molars, respectively. The arch wire 100 may be mounted on the dental arch using various devices including, for example, orthodontic brackets (not shown).

The arch wire 100 also includes an enlarged stop member 108 positioned at the center of the front section 102. The stop member 108 is designed to fit between brackets when the arch wire 100 is mounted on a patient's dental arch using brackets. The stop member 108 assures proper centering of the arch wire 100 and deters its slippage on the dental arch.

The arch wire 100 may comprise a nickel-titanium alloy, a nickel-chromium alloy, a nickel-cobalt alloy, alpha-titanium or beta-titanium. These materials are only exemplary and can be changed as desired. Preferably, the arch wire 100 should have superelasticity.

Unlike the arch wire 10 of FIG. 1, in which orthodontic forces vary in discrete steps, the arch wire 100 has a gradual force variation along the length of the wire.

Figure 4:
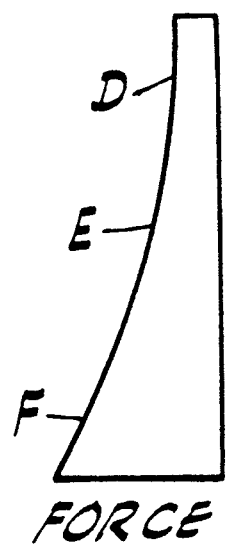
FIGS. 4-7 illustrate examples of possible force distributions along the FIG. 3 arch wire.
Figure 5:
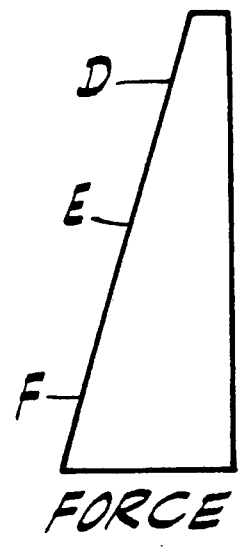
Figure 6:
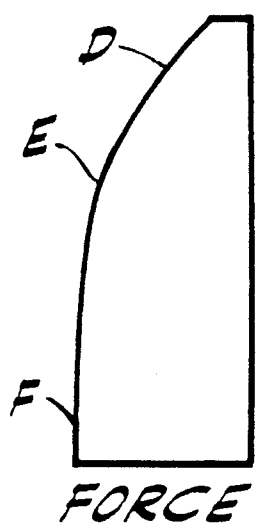
Figure 7:
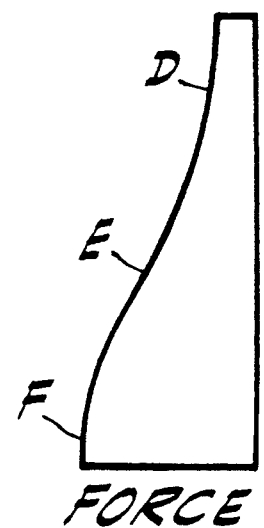

FIGS. 4-7 are examples of various force distributions along the arch wire 100 from the center of the front section 102 to the tip of one of the rear ends 106. Reference characters D, E and F shown in each of the FIGS. 4-7 generally correspond to the arch wire sections 102, 104 and 106, respectively. FIGS. 4-6 illustrate concave, linear and convex force distributions respectively. FIG. 7 illustrates both concave and convex force distribution. FIGS. 4-7 are examples of gradually varying orthodontic forces which may be changed for particular circumstances. For example, while each of the FIGS. 4-7 shows forces increasing from the center of the front section 102 to the tips of the end sections 106, an arch wire having decreasing forces from section 102 to section 106 may be provided to treat particular states of malocclusion.

An advantage of having gradually varying forces along the arch wire is that even with variations in a patient's dental arch and teeth size, the arch wire 100 will provide generally suitable forces for proper root movement.

Figure 8:
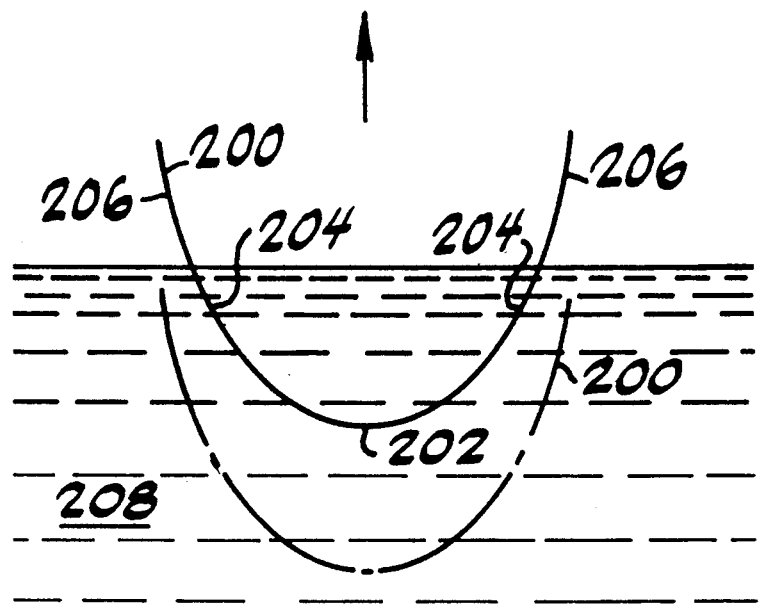
FIGS. 8 and 9 illustrate two methods of forming the FIG. 3 arch wire.
Figure 9:
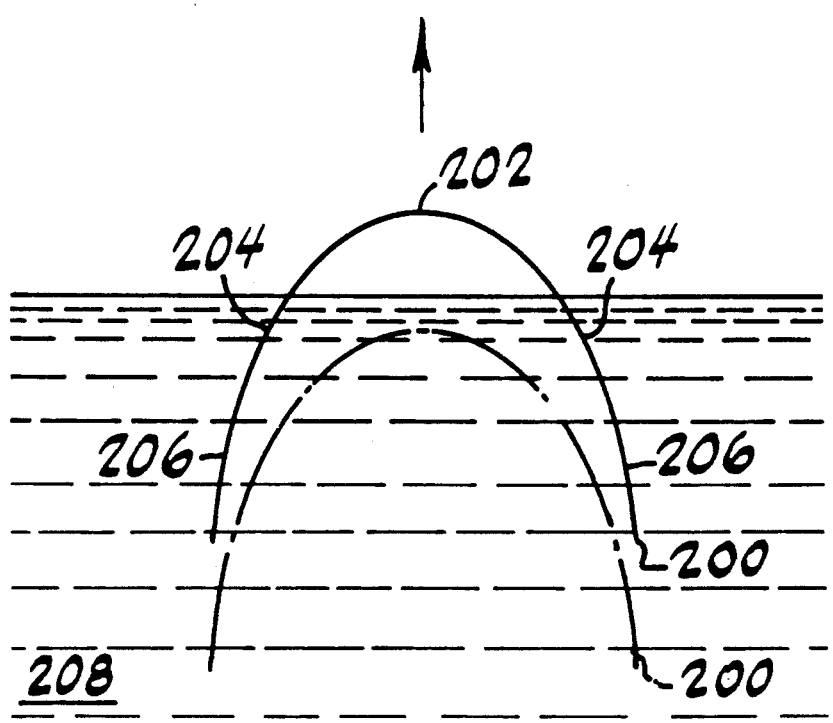

The arch wire 100 is provided with a gradually varying modulus of elasticity, enabling it to exert the gradually varying orthodontic forces. FIGS. 8 and 9 illustrate examples of two methods of forming an arch wire with a gradually varying modulus of elasticity by heat treatment. In FIG. 8, the first example, a wire member 200 is first formed into an arch shape by known methods like molding. The wire member 200 includes a front section 202, two middle sections 204 and two rear end sections 206, which to correspond generally to a patient's front teeth, bicuspids and molars, respectively. The member 200 is first subjected to a high load level by heat treatment and then immersed completely in a heated medium like a heated solvent 208. Then, after a prescribed period of time, the member 200 is gradually pulled out of the solvent 208. The two rear end sections 206 are removed first so that the front section 202 undergoes the longest period of heat treatment.

EXAMPLE

The solvent 208 is maintained at a temperature between 450°-550° C. (preferably 480°-520° C.). The member 200 having a high load level is completely submerged in the solvent 208 and then gradually and continually removed. The two end sections 206 are removed first from the solvent 208 after about 5 minutes. The front section 202 is eventually removed after about 60 to 80 minutes. The middle sections 204 are heated for periods greater than five minutes.

In FIG. 9, the second example of a method of forming the arch wire 100, a low load level is imparted by heat treatment to the member 200. The member 200 is immersed in the heating solvent 208 and then withdrawn gradually starting with the center of the front end section 202 and eventually ending with the two rear end sections 206.

EXAMPLE

The solvent 208 is maintained at temperature of 500° C. The wire member 200 having a low load level is completely immersed in the solvent 208 and then gradually and continually removed. The front section 202 is removed first after about 2-3 minutes. The two end sections 204 are eventually removed after 5-10 minutes.

If the solvent 208 is maintained at a temperature between 520° and 530° C., the front section 202 may be removed after one minute and the rear end sections 204 may be removed after 2-3 minutes.

In the methods shown in FIGS. 8 and 9, the portions of the member 200 withdrawn from the heating solvent 208 should be maintained in a cool state to reduce further effects from heat.

The method illustrated in FIG. 8 gradually decreases the load level of the central front section 202 under a comparatively long period of heat treatment, while the method shown in FIG. 9 gradually increases the load level of the two rear end sections 206 under a comparatively short period of heat treatment. Whichever method is used, it is possible to vary the intrinsic modulus of elasticity of the arch member 200 gradually by heat treatment. Thus, the orthodontic forces that can be exerted by the member 200 vary gradually without steps.

Figure 10:
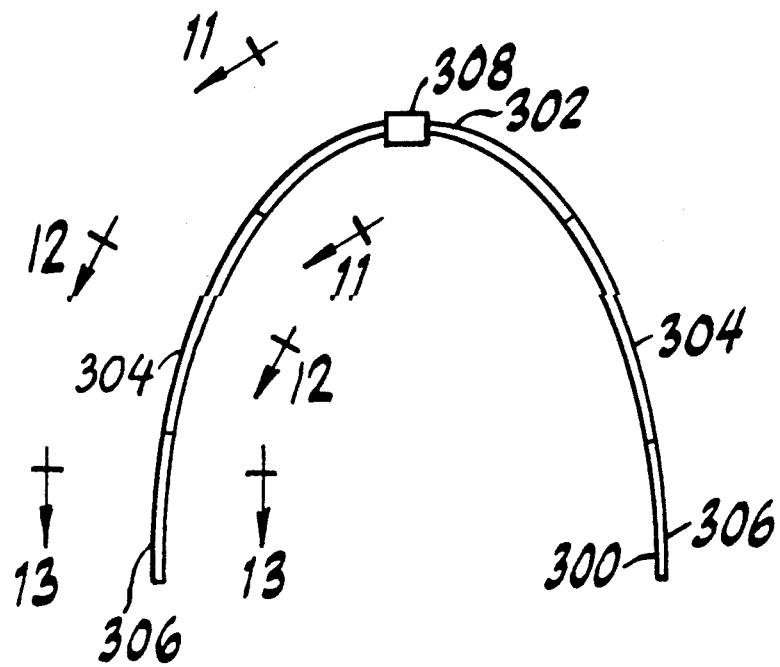
FIG. 10 is a top view of an orthodontic arch wire constructed in accordance with another embodiment of the invention.

FIG. 10 illustrates an arch wire 300 constructed in accordance with another embodiment of the invention. The arch wire 300 is similar to the arch wire 100 shown in FIG. 3 as it is heat treated so that there is a gradual variation in the modulus of elasticity and force magnitude along the wire. The arch wire 300 includes a front section 302, two middle sections 304 and two rear end sections 306 corresponding generally to a patient's front teeth, bicuspids and molars, respectively. A variety of force distributions may be present in the arch wire 300, including those discussed with reference to the arch wire 100.

Figure 11:
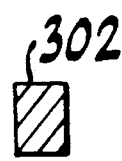
FIG. 11-13 are enlarged partial cross-sectional views taken generally along lines 11—11, 12—12 and 13—13, respectively of the arch wire shown in FIG. 10.
Figure 12:
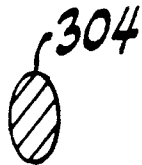
Figure 13:
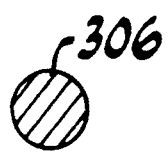

Each of the sections 302, 304 and 306 has a different cross-sectional shape. FIGS. 11–13 are enlarged partial cross-sectional views taken generally along lines 11—11, 12—12, and 13—13, respectively of the arch wire 300 in FIG. 10. As illustrated, the front section 302, the two middle sections 304 and the two rear end sections 306 have rectangular, elliptical and circular cross sections, respectively.

In addition to the advantages associated with having a gradually varying force distribution as previously described with respect to the arch wire 100, the arch wire 300 has additional advantages relating to its different sectional shapes. Having an angular sectional shape at the front section 302 enables the arch wire 300 to provide reliable directional correction of the front teeth. Having a round sectional shape in the rear end sections 306 allows smooth shifting of the arch wire 300 in the mesial and distal directions during treatment.

The desired sectional shapes of the arch wire 300 can be produced by subjecting an angular starting wire with a processing treatment like acid etching or electrolytic polishing.

Arch wire 300 also includes an enlarged stop member 308 positioned at the center the front section 302. The stop member 308 is designed to fit between brackets (not shown) when the arch wire 300 is mounted on a patient's dental arch. The stop member 308 assures proper centering of the arch wire 300 and deters its slippage on the dental arch.

Figure 14:
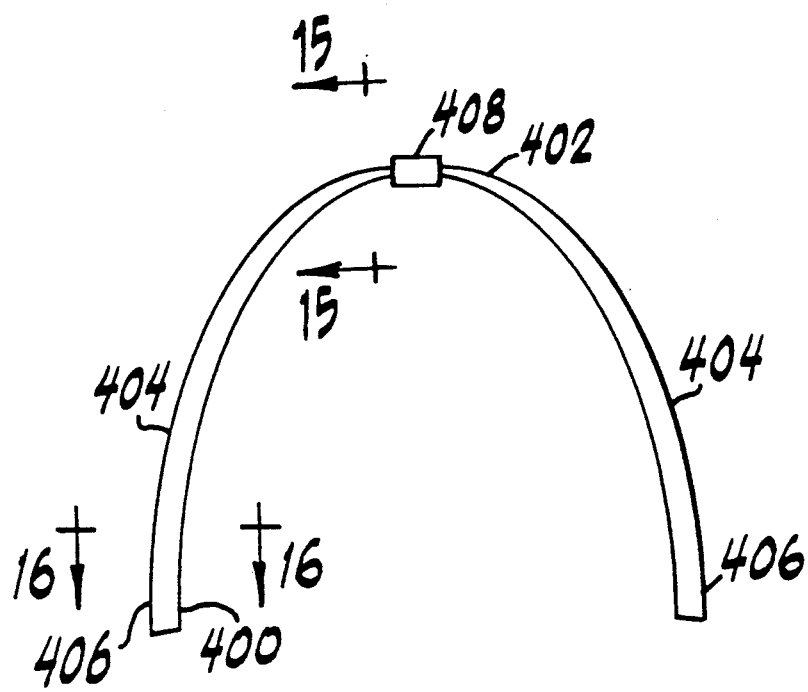
FIG. 14 is a top view of an orthodontic arch wire constructed in accordance with another embodiment of the invention.

FIG. 14 illustrates an arch wire 400 constructed in accordance with another embodiment of the present invention. The arch wire 400 includes a front section 402, two middle sections 404 and two end sections 406. The sections 402, 404 and 406 generally correspond to a patient's front teeth, bicuspids and molars, respectively. Like the arch wire 100 shown in FIG. 3, there is a gradual variation in the orthodontic forces along the length of the arch wire 400.

Figure 15:
FIGS. 15 and 16 are enlarged partial cross-sectional views taken generally along lines 15—15 and 16—16, respectively of the arch wire shown in FIG. 14.
Figure 16:
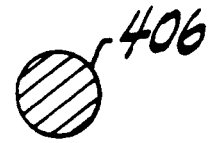

The arch wire 400 differs from arch wire 100 in that the cross-section of the arch wire 400 gradually increases in size from the center of the front section 402 to the tips of the end sections 406 as shown in an exaggerated manner in FIG. 14. FIGS. 15 and 16 are enlarged partial cross sectional views taken generally along lines 15—15 and 16—16, respectively of FIG. 14. FIGS. 15 and 16 show that the diameter of the arch wire 400 is larger at section 406 than it is at section 402.

The orthodontic forces that can be exerted by the arch wire 400 vary gradually along the wire as a result of the wire's gradually varying sectional size. The advantages of having gradually varying forces along the arch wire 400 are similar to those previously discussed with regard to the arch wire 100. A variety of force distributions may be present in the arch wire 400, including those discussed with regard to the arch wire 100.

An arch wire having a gradual variation in its sectional size may be produced by subjecting a starting wire to processes like acid etching or electrolytic polishing. Alternatively, the starting wire may be formed into the desired shape by a rolling process.

The arch wire 400 also includes a stop member 408 positioned at the center of the front section 402. The stop member 408 enables proper centering and prevents slippage of the arch wire during patient treatment.

While each of the arch wires shown thus far comprises a single member wire, it is possible to use a twisted wire such as a twisted nickel-titanium alloy wire.

Although the present invention has been described with respect to specific, preferred embodiments, various changes and modifications may be suggested to one skilled in the art, and it is intended that the present invention encompasses such changes and modifications as fall within the scope of the appended claims.

I claim:

1. An orthodontic arch wire for applying corrective forces to a patient's dental arch, comprising an arch shape wire which has been treated to exhibit properties which exert forces on the dental arch that gradually and continuously vary in magnitude along substantially the length of the arch wire.

2. The orthodontic arch wire of claim 1, wherein said arch shaped wire comprises a front section, two middle sections and two end sections corresponding generally to a patient's front teeth, bicuspids and molars, respectively and wherein said forces exertable by said wire gradually increase from said front section to said end sections.

3. The orthodontic arch wire of claim 1, wherein said arch shaped wire has a gradually varying modulus of elasticity along the wire corresponding to the gradually varying forces exertable by said arch shaped wire.

4. The orthodontic arch wire of claim 1, wherein said arch shaped wire has a gradually varying cross-sectional area corresponding to the gradually varying forces exertable by said arch shaped wire.

5. The orthodontic arch wire of claim 4, wherein said arch shaped wire has a round cross-sectional shape.

6. The orthodontic arch wire of claim 4, wherein said arch shaped wire has an angular cross-sectional shape.

7. The orthodontic arch wire of claim 4, wherein said arch shaped wire comprises a front section generally corresponding to a patient's front teeth and two rear end sections generally corresponding to the patient's molars and the cross sectional area of said arch shaped wire gradually decreases from said rear end sections to said front section.

8. The orthodontic arch wire of claim 1, wherein said arch shaped wire has a rectangular cross section at one portion of the wire and a circular cross section at another portion of the wire.

9. The orthodontic arch wire of claim 1, wherein said arch shaped wire has a front section, two middle sections and two end sections generally corresponding to a patient's front teeth, bicuspids and molars, respectively and wherein said front section has a rectangular cross section, said middle sections have an elliptical cross section and said end sections have round cross sections.

10. The orthodontic arch wire of claim 1, wherein said arch shaped wire has superelasticity.

11. The orthodontic arch wire of claim 1, wherein said arch shaped wire comprises a nickel-titanium alloy.

12. The orthodontic arch wire of claim 1, wherein said arch shaped wire comprises a nickel-chromium alloy.

13. The orthodontic arch wire of claim 1, wherein said arch shaped wire comprises a nickel-cobalt alloy.

14. The orthodontic arch wire of claim 1, wherein said arch shaped wire comprises alpha-titanium.

15. The orthodontic arch wire of claim 1, wherein said arch shaped wire comprises beta-titanium.

16. The orthodontic arch wire of claim 1, wherein said arch shaped wire comprises a twisted wire.

17. The orthodontic arch wire of claim 1, wherein said arch shaped wire comprises a front section and an enlarged stop member positioned on said front section for enabling proper centering of said wire on the dental arch.

18. A method of forming a gradually variable force orthodontic arch wire, comprising the steps of:
   subjecting an arch shaped wire to a heated medium; and
   gradually and substantially continuously removing the arch shaped wire from the heated medium, thereby causing a gradual variation in the intrinsic modulus of elasticity along the arch shaped wire.

19. The method of claim 18, wherein said step of subjecting the arch shaped wire to a heated medium comprises immersing the arch shaped wire in a heated solvent.

20. An orthodontic arch wire, comprising an arch shaped wire having a gradually and substantially continuously varying modulus of elasticity along the length of the wire for enabling the arch wire to exert gradually and substantially continuously varying orthodontic forces along the length of the wire.

21. The arch wire of claim 20, wherein said arch shaped wire has a front section, two middle sections and two end sections generally corresponding to a patient's front teeth, bicuspids and molars, respectively and wherein said front section has a rectangular cross section and said end sections have round cross sections for improved directional correction and smooth shifting during use.

22. The arch wire of claim 20, wherein said arch shaped wire includes a front section generally corresponding to a patient's front teeth and wherein said front section includes an enlarged portion for centering the arch wire on the teeth.

23. An orthodontic arch wire, comprising an arch shaped wire having a gradually and continuously varying cross-sectional area along the length of the wire for enabling the arch wire to exert orthodontic forces that gradually change in magnitude along the length of the wire.

24. The orthodontic arch wire of claim 23, wherein said arch shaped wire includes a front section generally corresponding to a patient's front teeth and wherein said front section includes a stop member at the middle thereof for centering the arch wire.

25. The orthodontic arch wire of claim 23, wherein said arch shaped wire is superelastic.

26. An orthodontic arch wire for applying gradually varying orthodontic forces on a patient's dental arch, comprising a superelastic arch shaped wire having a gradually and substantially continuously varying modulus of elasticity along the length of the wire for enabling the orthodontic arch wire to exert gradually and substantially continuously varying forces on the dental arch.

27. An orthodontic arch wire for orthodontic treatment of misaligned teeth in a patient's dental arch, comprising a superelastic wire shaped to correspond to the dental arch, said wire having a gradually and substantially continuously varying modulus of elasticity for exerting corrective forces on the teeth with the forces gradually and substantially continuously varying in magnitude along the length of the wire.

28. An orthodontic arch wire for applying corrective forces to a patient's dental arch, comprising an arch shaped wire having integrally formed front, middle, and end sections corresponding generally to a patient's front teeth, bicuspids and molars, respectively, said front section including a center portion and said end sections each including a tip, said wire being treated to exhibit properties which exert forces on the dental arch that gradually and continuously increase in magnitude along the wire from said center portion to said tips, said wire being superelastic and comprising nickel-titanium.

* * * * *